United States Patent [19]

Williams, III

[11] 4,273,712

[45] Jun. 16, 1981

[54] METHOD FOR MAKING AROMATIC ETHER IMIDES

[75] Inventor: Frank J. Williams, III, Scotia, N.Y.

[73] Assignee: General Electric Company, Schenectady, N.Y.

[21] Appl. No.: 37,441

[22] Filed: May 9, 1979

[51] Int. Cl.³ .......................................... C07D 209/48
[52] U.S. Cl. ........................... 260/326 N; 260/326 R; 260/326 S; 260/326 HL
[58] Field of Search ........... 260/326 N, 326 R, 326 S, 260/326 HL; 568/723, 724

[56] References Cited

U.S. PATENT DOCUMENTS

| | | | |
|---|---|---|---|
| 3,852,242 | 12/1974 | White | 528/723 |
| 3,957,862 | 5/1976 | Heath et al. | 562/468 |
| 4,048,190 | 9/1977 | Johnson et al. | 260/326 N |

OTHER PUBLICATIONS

C. Starks, J. Amer. Chem. Soc., 93:1, (1971), pp. 195–199, Phase-Transfer Catalysis I. Heterogeneous Reactions Involving Anion Transfer by Quaternary Ammonium and Phosphonium Salts.

*Primary Examiner*—Donald G. Daus
*Assistant Examiner*—M. C. Eakin
*Attorney, Agent, or Firm*—William A. Teoli; James C. Davis, Jr.

[57] ABSTRACT

A method for making aromatic ether imides is provided by effecting the displacement of reactive radicals on a phthalimide nucleus with a mono- or bis-alkali metal phenoxide in the presence of a nonpolar solvent and a phase transfer catalyst, such as a tetra-ammonia salt. The aromatic ether imides made by the present invention are useful intermediates for making aromatic ether anhydrides and aromatic bis(ether anhydrides).

15 Claims, No Drawings

METHOD FOR MAKING AROMATIC ETHER IMIDES

CROSS REFERENCES TO RELATED APPLICATIONS

Reference is made to copending applications of Tohru Takekoshi Ser. No. 37,440, now U.S. Pat. No. 4,202,993 for Method for Making Substantially Anhydrous Alkali Metal Bisphenol Salts and Frank J. Williams, III et al Ser. No. 37,442, for Method for Making Alkali metal Bisphenoxide Salts and Bisimides Derived Therefrom, where both applications are filed concurrently herewith and assigned to the same assignee as the present invention.

BACKGROUND OF THE INVENTION

The present invention relates to a method for making aromatic ether imides by effecting the condensation of a phenoxide salt with a nuclear-substituted phthalimide in the presence of a nonpolar solvent and a phase transfer catalyst. More particularly, the present invention relates to a method for making an aromatic ether phthalimide or an aromatic bis (ether phthalimide).

Prior to the present invention, methods involving the condensation of an alkali metal phenoxide with a nuclear substituted phthalimide as shown by Heath et al U.S. Pat. Nos. 3,879,428, 3,957,862 and 3,956,320, assigned to the same assignee as the present invention, or Meyers U.S. Pat. No. 3,965,125, were generally based on the use of a dipolar aprotic solvent to facilitate reaction. Those skilled in the art know that it is often economically unattractive to effect the synthesis of various organic materials using dipolar aprotic solvents because such solvents are expensive and often subject to a variety of chemical side reactions which render them useless for recycling.

The present invention is based on the discovery that aromatic ether imides of the formula,

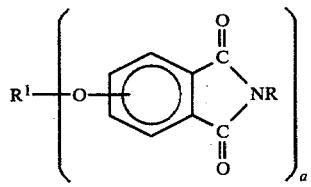

(1)

can be made without the use of a dipolar aprotic solvent, by effecting the reaction between the alkali metal phenoxide salt or diphenoxide salt and the nuclear substituted phthalimide in a nonpolar organic solvent and in the presence of a phase transfer catalyst, where R is a monovalent radical selected from hydrogen, a $C_{(1-8)}$ alkyl radical and $C_{(6-13)}$ aryl radical, $R^1$ is a $C_{(6-30)}$ aromatic organic radical, and a is an integer equal to 1 or 2, and when a is 1, $R^1$ is monovalent and when a is 2, $R^1$ is divalent.

STATEMENT OF THE INVENTION

There is provided by the present invention, a method for making aromatic ether imides of formula (1), which comprises (A) heating a substituted phthalimide of the formula,

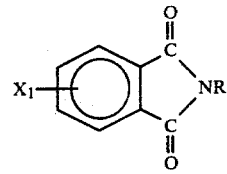

(2)

and an alkali metal phenoxide salt of the formula,

(3)

in the presence of a nonpolar organic solvent and an effective amount of a phase transfer catalyst of the formula,

(4)

(B) agitating the resulting mixture with a precipitating or extractive organic solvent for the resulting bisimide or allowing the mixture to cool and (C) recovering the bisimide from the mixture of (B), where R, $R^1$ and a is as previously defined, M is an alkali metal ion, $R^2$ is a $C_{(1-16)}$ alkyl radical and $C_{(6-13)}$ aromatic radical, Q is a group Va element selected from N and P, Y is a halogen or carbethoxy radical and $X_1$ is a radical selected from nitro and halo.

Radicals included by R, are for example, phenyl, tolyl, xylyl, naphthyl, chlorophenyl, bromonaphthyl, etc., and alkyl radicals such as methyl, ethyl, propyl, etc. Radicals included by $R^1$ are the aforementioned monovalent aromatic radicals included by R, divalent aromatic radicals, such as phenylene, tolyene, naphthylene, and $R^1$ more particularly includes

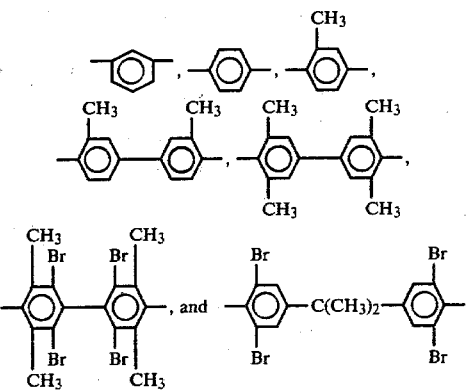

and divalent organic radicals of the general formula,

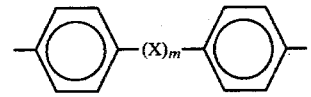

where X is a member selected from the class consisting of divalent radicals of the formula,

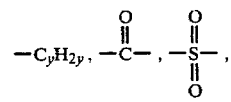

—O—, and —S—, where m is 0 or 1, y is a whole number from 1 to 5.

Radicals included by $R^2$ are, for example, propyl, butyl, pentyl, hexyl, heptyl, octyl and phenyl. M is more particularly sodium, potassium, lithium, rubidium, etc; Y is more particularly, chloro, bromo, iodo, acetato, etc.

Included by the substituted phthalimides of formula (2), are for example, 4-nitro,N-phenylphthalimide; 3-nitro,N-phenylphthalimide; 4-nitro,N-methylphthalimide; 3-nitro,N-methylphthalimide; 4-fluoro,N-methylphthalimide; 3-fluoro,N-methylphthalimide; 4-chloro,N-methylphthalimide; 3-chloro,N-methylphthalimide, etc. These substituted phthalimides can be made by standard procedures, such as effecting reaction between substantially equal mols of the corresponding phthalic anhydride and an organic amine in the presence of refluxing acetic acid. Included by the organic amines which can be used, are, for example, aniline, toluidene, etc., methylamine, ethylamine, etc. Included by the phase transfer catalysts of formula (4) are, for example, tetrabutylammonium bromide, tetrapropylammonium bromide, tetrabutylammonium chloride, tetrabutylammonium fluoride, tetrabutylammonium acetate, tetrahexylammonium chloride, tetraheptylammonium chloride. Aliquat 336 phase transfer catalyst (methyltrioctylammonium chloride, manufactured by the General Mills Company), tetrabutylphosphonium bromide, tetraphenylphosphonium bromide, tetraphenylammonium bromide, tetrabutylphosphonium chloride, etc.

The alkali metal salts of formula (3) can be made by various procedures, including the flash evaporation of bisphenoxide alkali metal salt hydrate or an aqueous slurry thereof, as shown by the copending application Ser. No. 37,440, now U.S. Pat. No. 4,202,993 of Tohru Takekoshi, or by azeotroping water from an aqueous mixture of bisphenoxide alkali metal salt and toluene as shown by copending application Ser. No. 37,442 of Frank J. Williams, III et al. Additional procedures are shown in White U.S. Pat. No. 3,852,242, assigned to the same assignee as the present invention.

Some of the alkali metal salts of the above-described alkali phenoxides of formula (3) are sodium and potassium salt phenols, such as phenol, cresol, naphthol, etc.; dihydric phenols, for example,
2,2-bis(2-hydroxyphenyl)propane;
2,4'-dihydroxydiphenylmethane;
bis(2-hydroxyphenyl)methane;
2,2-bis-(4-hydroxyphenyl)propane hereinafter identified as "bisphenol-A" or "BPA";
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenylsulfoxide;
4,4'-dihydroxydiphenylsulfide;
hydroquinone;
resorcinol;
3,4'-dihydroxydiphenylmethane;
4,4'-dihydroxybenzophenone; and
4,4'-dihydroxydiphenylether.

In the practice of the invention, reaction is effected between the substituted phthalimide and the phenoxide salt, which hereinafter will signify either the mono- or dihydric phenol salt in the presence of a nonpolar solvent and an effective amount of a phase transfer catalyst, followed by the recovery of the resulting "ether phthalimide" which hereinafter can signify either aromatic ether phthalimide, or aromatic bis(ether phthalimide). It is preferred to effect reaction under substantially anhydrous conditions, although small amounts of moisture can be tolerated..

Temperatures at which reaction between the phenoxide salt and the substituted phthalimide can be effected are in the range of about between 25° C. to 150° C., and preferably a temperature between 100°–120° C. Any nonpolar organic solvent which does not react with the reactants during the formation of the ether phthalimide can be used in the reaction. Some of the nonpolar organic solvents are, for example, toluene benzene, chlorobenzene, xylene, tetrahydrofuran, acetonitrile, octane, etc.

Experience has shown that the reaction can best be run using a solids concentration in the range of between about 5% to 150% by weight of solids, based on the total volume of non-polar solvent used, and preferably from between about 85–95% by weight. Preferably, equivalent amounts of the phenoxide salt and a substituted phthalimide can be used, while higher or lower amounts of either reactant will not substantially interfere with the formation of the desired ether phthalimide. In preparing the aromatic bis(ether phthalimide) there is preferably used about 2 mols of the substituted phthalimide, per mol of the bisphenoxide salt. The phase transfer catalyst as previously defined, can be utilized at from 0.005 equivalent to 2 equivalents of catalyst, per equivalent of alkali bisphenoxide and preferably from 0.02 to 0.05 equivalent.

The ether phthalimide can be recovered from the reaction mixture by a variety of procedures. One procedure, for example, can be by allowing the reaction mixture to cool, followed by recovery of the ether phthalimide by filtration. It is preferred, however, because of the partial solubility of the ether phthalimide in various nonpolar organic solvents, to precipitate the ether phthalimide by use of a precipitating solvent, for example, methanol, followed again by a standard recovery technique, such as filtration. Alternatively, the ether phthalimide can be extracted from the reaction mixture with a better solvent such as methylene chloride, chloroform, etc., washed with water to effect removal of the inorganic salts, and recovered by the removal of the organic solvent under reduced pressure.

Experience has shown that the phase transfer catalysts and byproducts of the reaction can be recycled directly for further use in the production of ether phthalimide in accordance with the practice of the invention. For example, in the situation where the reaction mixture is allowed to cool to room temperature to effect the separation of ether phthalimide, the filtrate can be reused as a source of the phase transfer catalyst and the nonpolar organic solvent. In instances where a precipitating solvent is employed to effect the separation of ether phthalimide, the filtrate can be evaporated to dryness to recover the phase transfer catalyst which can be recycled.

The following examples are given by way of illustration and not by way of limitation. All parts are by weight and all mixtures are agitated, for example, stirred during reflux.

EXAMPLE 1

Several mixtures were prepared having tetra-butyl ammonium bromide phase transfer catalyst at different weight levels in combination with 0.9957 part of sodium 4-methylphenoxide, 1.578 part of 4-nitro-N-methylphthalimide, 0.4202 part of ortho-terphenyl (as an internal standard) and 14 parts of toluene. Additional mixtures were prepared having the same ingredients at the same weight levels except different phase transfer catalysts were substituted for tetra-butyl ammonium bromide. Mixtures were also prepared free of phase transfer catalyst, having as a solvent either toluene, or a dipolar aprotic solvent. The various mixtures were then refluxed to produce ether phthalimide of the formula,

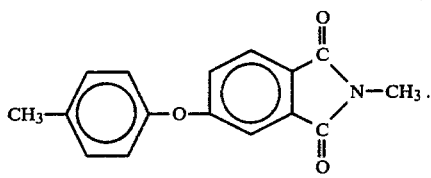

The results are shown in Table I, where "PTC" is phase transfer catalyst, DMSO is dimethylsulfoxide, and DMF is dimethylformamide.

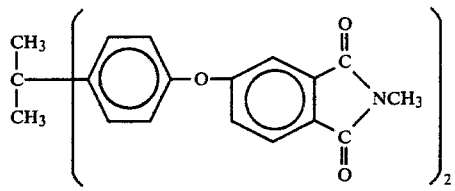

having a melting point of 145°–147° C.

EXAMPLE 3

A mixture of 6.01 parts of the sodium salt of bisphenol-A, 9.15 parts of 4-nitro-N-methylphthalimide, 1.78 part of tetrabutylammonium bromide and about 39 parts of toluene was refluxed under nitrogen for 40 minutes. The mixture was then allowed to cool to ambient conditions and then diluted with about 96 parts of methanol. A precipitate was formed which was recovered by filtration and washed with methanol. There was obtained 11.2 parts of product or a 93% yield having a melting point of 146.5°–148° C. Based on method of preparation the product was the ether phthalimide of formula (2). The filtrate and the washes were combined and concentrated and the resulting solid was dried under reduced pressure at 105° C. for ½ hour.

The mixture of 5.9 parts of the sodium salt of bisphenol-A, 8.98 parts of 4-nitro-N-methylphthalimide, 5

TABLE I

| | | | | % Yield of Ether Phthalimide (Reflux Time in Hr.) | | | | |
|---|---|---|---|---|---|---|---|---|
| P.T.C. | Amount | Solvent | Temp. | 0.5 | 1.0 | 2.0 | 3.0 | 6.0 |
| $Bu_4 N^\oplus Br^\ominus$ | 0.1 eq. | Toluene | 110° (reflux) | 68 | 73 | 85 | 93 | 96 |
| $Bu_4 N^\oplus Br^\ominus$ | 1.0 eq. | " | " | 95 | 94 | 95 | 99 | |
| $Et_3N^\oplus CH_2C_6H_5Br^\ominus$ | 0.1 eq. | " | " | 9 | 13 | 13 | 13 | 13 |
| Aliquat 336[a] | 0.1 eq. | " | " | 17 | 29 | 39 | 42 | 46 |
| Adogen 464[b] | 0.1 eq. | " | " | 30 | 39 | 47 | 52 | 57 |
| $(n\text{-heptyl})_4N^\oplus Cl^\ominus$ | 0.1 eq. | " | " | 53 | 66 | 72 | 78 | 82 |
| None | | " | 110° (reflux) | 0 | 0 | 0 | 0 | 0[c] |
| None | | DMSO | 68° | 94 | | | | |
| None | | DMF | 68° | 93 | | | | |

[a] Methyltricapryl ammonium chloride (TM of General Mills Company)
[b] Methyltrialkyl ($C_8$-$C_{10}$) ammonium chloride (TM of Ashland Chemical Company)
[c] Yield after 24 hours was still 0%

The above results show that no reaction occurred in the absence of the phase transfer catalyst when a nonpolar solvent was used.

EXAMPLE 2

Reaction was effected between equal molar amounts of bisphenol-A and sodium methoxide in anhydrous methanol. A mixture of 1.99 part of the resulting sodium bisphenoxide salt, 3.02 part of 4-nitro-N-methylphthalimide, 4.71 parts of tetrabutylammonium bromide which was 2 equivalents, and about 21 parts of toluene, was heated at reflux under nitrogen for 22 hours. The reaction mixture was cooled to room temperature and was extracted with a mixture of methylene chloride and 1.2 normal HCl. The resulting organic solution was dried and concentrated. The resulting mixture was stirred with methanol and filtered resulting in 2.35 parts of an ether phthalimide of the formula, parts of the catalyst residue recovered above and about 37 parts of toluene was heated at reflux for 40 minutes. There was obtained a 95% yield of the ether phthalimide of bisphenol-A as previously defined having the same melting point. The filtrate and the washings were again recovered and concentrated following the above procedure to salvage the phase transfer catalyst for further use in the production of aromatic ether phthalimide. It was found that the yield of the ether phthalimide remained substantially unchanged over several additional runs using the same recycled catalyst.

EXAMPLE 4

An evaluation of the effectiveness of various phase transfer catalysts was made to determine the optimum catalyst and the optimum concentration for effecting the nitro displacement of 4-nitro-N-methylphthalimide with sodium cresoxide in toluene. There was utilized an equal molar amount of the reactants in the mixture and the phase transfer catalyst was utilized at 0.1 equivalent, based on the mols of the sodium phenoxide salt employed. The weight percent yields of ether phthalimide are listed under "Toluene refluxing time in Hr." and "PTC" is defined as in Example 1.

TABLE II

| P T C | (Toluene refluxing time in Hr.) | | | | |
|---|---|---|---|---|---|
| | 0.5 | 1.0 | 2.0 | 3.0 | 6.0 |
| None | 0 | 0 | 0 | 0 | 0 |
| $(CH_3)_4N^{\oplus}Br^{\ominus}$ | 0.6 | 4 | 13 | 20 | 27 |
| $(C_2H_5)_4N^{\oplus}Br^{\ominus}$ | 3 | 4 | 8 | 13 | 32 |
| $(n-C_3H_7)_4N^{\oplus}Br^{\ominus}$ | 49 | 63 | 70 | 75 | 76 |
| $(C_4H_9)_4N^{\oplus}Br^{\ominus}$ | 68 | 73 | 85 | 93 | 96 |
| $(C_4H_9)_4N^{\oplus}Cl$ | 72 | 74 | 78 | 81 | 82 |
| $(C_4H_9)_4N^{\oplus}I^{\ominus}$ | 24 | 32 | 40 | 45 | 54 |
| $(C_4H_9)_4N^{\oplus}F^{\ominus}$ | 56 | 70 | 74 | 82 | 93 |
| $(C_4H_9)_4N^{\oplus}F^{\ominus}(.XH_2O)$ | 11 | 17 | 30 | 36 | 48 |
| $(C_4H_9)_4N^{\oplus}OAc^{\ominus}$ | 20 | 27 | 36 | 39 | 50 |
| $(Hexyl)_4N^{\oplus}Cl^{\ominus}$ | 47 | 51 | 61 | 67 | 74 |
| $(Heptyl)_4N^{\oplus}Cl^{\ominus}$ | 53 | 66 | 72 | 78 | 82 |
| Aliquat 336 | 17 | 29 | 39 | 42 | 46 |
| Adogen 464 | 30 | 39 | 47 | 52 | 57 |
| $(C_2H_5)_3N^{\oplus}CH_2(C_6H_5)Br^{\ominus}$ | 9 | 13 | 13 | 13 | 13 |
| $CH_3(CH_2)_{15}N^{\oplus}(CH_3)_3Br^{\ominus}$ | 15 | 17 | 24 | 25 | 32 |
| $(C_4H_9)_4P^{\oplus}Br^{\ominus}$ | 17 | 21 | 25 | 28 | 33 |
| $(C_6H_5)_3P^{\oplus}CH_3Br^{\ominus}$ | 1 | 2 | 2 | 2 | 4 |
| $(C_6H_5)_3P^{\oplus}CH_2(C_6H_5)Br^{\ominus}$ | 2 | 2 | 2 | 3 | 5 |
| $(C_4H_9)_4P^{\oplus}Cl^{\ominus}$ | 20 | 30 | 33 | 38 | 44 |
| Dibenzo-18-crown-6 | 19 | 27 | 35 | 50 | 56 |
| 15-crown-15 | 49 | 54 | 62 | 64 | 68 |
| $(C_4H_9)_4N^{\oplus}OAc^{\ominus}(.XH_2O)$ | 3 | 9 | 21 | 27 | 42 |

The above results show that tetrabutylammonium bromide and tetrabutylammonium fluoride provide the highest weight percent yields of ether phthalimide.

EXAMPLE 5

A mixture of 62.54 parts of anhydrous disodium bisphenol-A, 94.9 parts of 4-nitro-N-methylphthalimide, 18.51 parts of tetrabutylammonium bromide and 366 parts of toluene was heated at reflux for 1.5 hour. The mixture was cooled to 25° C. and diluted with 1200 parts of methanol. There was obtained a precipitate which was collected, reslurried with methanol and dried to provide 94 parts of product which represented a 94% yield. Based on method of preparation, the product was 2,2-bis[4-(N-methylphthalimide-4-oxy)phenyl]-propane.

The above reaction was repeated using increasing solids levels and decreasing amounts of catalyst. The following results were obtained, where the amounts indicated are in parts, unless otherwise shown, "BPA" is bisphenoxide ion, "4-NPI" is 4-nitrophthalimide, and BPA-BI is the bisetherimide named above.

TABLE III

| BPA= | 4-NPI | Toluene | Conc. (%) | Moles $Bu_4N^+ Br^-$ Per 1 mole BPA= | BPA-BI | % Yield BPA-BI |
|---|---|---|---|---|---|---|
| 62.54 | 94.90 | 366 | 37 | 0.25 | 118.1 | 94 |
| 5.42 | 8.20 | 31 | 38 | 0.11 | 10.0 | 92 |
| 8.37 | 12.65 | 30 | 60 | 0.055 | 16.1 | 96 |
| 8.26 | 12.50 | 20 | 90 | 0.022 | 15.7 | 95 |
| 6.80 | 10.29 | 16 | 95 | 0.011 | 10.9 | 81 |

The above results show that increasing solids concentration can markedly influence the amount of catalyst required.

EXAMPLE 6

A mixture of 6.01 parts of the disodium salt of bisphenol-A, 9.15 parts of 4-nitro-N-methylphthalimide, different amounts of tetrabutylammonium bromide and about 38 parts of toluene, which amounted to about 35% solids, was refluxed under a nitrogen atmosphere for a period of form 0.5 to 6 hours. The results shown in Table IV illustrate the importance of catalyst level at a given solids concentration.

TABLE IV

| Eq. P.T.C./1 Eq. BPA= | % Displacement |
|---|---|
| 2 | 92 |
| 1 | 94 |
| 0.8 | 89 |
| 0.6 | 93 |
| 0.4 | 92 |
| 0.2 | 93 |
| 0.1 | 63 |

EXAMPLE 7

A mixture of 1.1301 part of bisphenol-A dianion, 1.5013 parts of 4-fluoro-N-methylphthalimide, 0.3346 parts $Bu_4N^+Br^-$ (0.25 eq./eq. bisphenol-A dianion) and 7.7 parts of toluene amounting to 30% solids was stirred under nitrogen at reflux for 2½ hours. The reaction mixture was cooled to 25° C., diluted with methanol and filtered to give 1.91 part or an 86% yield of product having a melting point of 147°–149° C. Based on method of preparation, the product was 2,2-bis[4-(N-methylphthalimide-4-oxy)phenyl]propane.

Additional bisimides were prepared utilizing phthalimides of the formula,

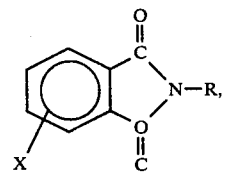

in a similar manner as shown in Table V below:

TABLE V

| X | R | Time (hr.) | BPA Salt % Yield | MP °C. (Lit) |
|---|---|---|---|---|
| 4-NO$_2$ | C$_6$H$_5$ | 1 hr. | 86 | 211–212 (211–213) |
| 3-NO$_2$ | C$_6$H$_5$ | 1 hr. | 86 | 203–204.5 (203–204.5) |
| 3-NO$_2$ | CH$_3$ | 1 hr. | 89 | 206.5–207.5 |

EXAMPLE 8

Example 6 was repeated using 0.25 equivalents of tetrabutylammonium chloride in place of the bromide to obtain a 92% yield of the desired bisimide. In a similar fashion, the reaction was repeated using 0.25 equivalents of Aliquat 336 to give a 60% yield of 2,2-bis[4-(N-methylphthalimide-4-oxy)phenyl]-propane.

EXAMPLE 9

Anhydrous bisphenol-A disodium salt was generated by azeotropically removing water from the hexahydrate. A mixture of 11.81 parts of the bisphenol-A hexahydrate and 35 parts of toluene was refluxed until all traces of water had been removed by azeotropic distillation. To this mixture was added 12.33 parts of 4-nitro-N-methylphthalimide and 1.06 part of tetrabutylammonium bromide. The reaction mixture was heated at reflux for 1 hour and worked up as described in Example 5 to give 15.1 parts (92% yield) of the corresponding bisimide.

The above reaction is repeated, except that xylene is used in place of toluene. There is obtained substantially similar results.

Toluene is used as an azeotroping solvent to make the above described bisimide, by the same procedure, except that the mixture is allowed to cool to 25° C. and filtered. The resulting solid is thereafter washed with 5 ml of hot toluene and methanol to obtain a high yield of the desired bisimide.

EXAMPLE 10

A mixture of 2.95 parts of bisphenol-A dianion, 4.67 parts of 4-nitro-N-methylphthalimide, 0.697 g of Bu₄N⁺Br⁻ and 43.3 parts of toluene was heated at reflux under nitrogen for 4 hours. The reaction mixture was cooled to 25° C. and diluted with 266 parts of methylene chloride. The solution was extracted with water and the organic solution was dried and concentrated to give after a methanol and water wash, 6.6 parts or a 95% yield of the corresponding bisimide.

Although the above examples are directed to only a few of the parameters which can be used in the practice of the method of the present invention, it should be understood that the present invention is directed to a much broader method of making aromatic ether imides as shown by the disclosure preceding these examples.

What I claim as new and desire to secure by Letters Patent of the United States is:

1. A method for making aromatic ether imides of the formula,

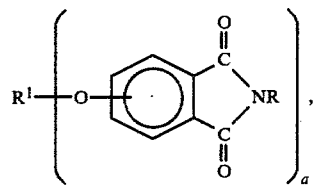

which comprises
(A) heating at 25° to 150° C. under substantially anhydrous conditions, a mixture consisting essentially of substituted phthalimide of the formula,

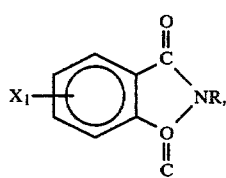

and an alkali metal phenoxide salt of the formula,

in the presence of a nonpolar organic solvent and an effective amount of a phase transfer catalyst of the formula,

(B) agitating the resulting mixture with a precipitating or extractive organic solvent for the resulting bisimide or allowing the mixture to cool and
(C) recovering the bisimide from the mixture of (B), where R is a monovalent group selected from hydrogen, a $C_{(1-8)}$ alkyl group, a $C_{(6-13)}$ aryl group and a and a $C_{(6-13)}$ haloaryl group, $R^1$ is an aromatic group selected from the group consisting of a $C_{(6-30)}$ aromatic carbocyclic group, a halogenated $C_{(6-30)}$ aromatic carbocyclic group and an alkylated $C_{(6-30)}$ aromatic carbocyclic group and a divalent organic group of the formula,

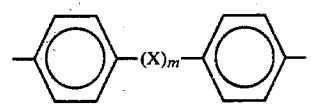

where X is a member selected from the group consisting of divalent groups of the formula,

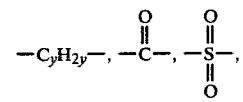

—O—, and —S—, m is 0 or 1, y is a whole number from 1 to 5, $R^2$ is selected from a $C_{(1-16)}$ alkyl radical and a $C_{(6-13)}$ aromatic carbocyclic radical, Q is a Group Va element selected from N and P, Y is a halogen or carbethoxy radical, $X_1$ is a member selected from the group consisting of nitro and halo, and a is an integer equal to 1 or 2, and when a is 1, $R^1$ is monovalent and when a is 2, $R^1$ is divalent.

2. A method in accordance with claim 1, utilizing an alkali metal monophenoxide salt.

3. A method in accordance with claim 1, utilizing an alkali metal diphenoxide salt.

4. A method in accordance with claim 1, where the alkali metal salt is the anhydrous disodium salt of bisphenol-A.

5. A method in accordance with claim 1, where the alkali metal phenoxide salt is made by azeotroping water from a mixture of toluene and the hydrated form of the alkali metal phenoxide salt.

6. A method in accordance with claim 1, where the alkali metal phenoxide salt is formed in situ from an aqueous mixture of the alkali metal hydroxide and the corresponding phenol.

7. A method in accordance with claim 1, where the alkali metal phenoxide salt is made from a mixture of an alkali metal alkoxide and the corresponding monohydric or dihydric phenol.

8. A method in accordance with claim 1, where Y in the phase transfer catalyst is chloride.

9. A method in accordance with claim 1, where the phase transfer catalyst is methyl tricapryl ammonium chloride.

10. A method in accordance with claim 1, where the substituted phthalimide is 3-nitro-N-methylphthalimide.

11. A method in accordance with claim 1, where the substituted phthalimide is 4-fluoro-N-methyl phthalimide.

12. A method in accordance with claim 1, where the substituted phthalimide is a nitro-N-methyl or N-phenyl phthalimide.

13. A method in accordance with claim 1, where the alkali metal phenoxide is an alkali bisphenoxide of a dihydric sulfone.

14. A method in accordance with claim 1, where the alkali metal phenoxide is an alkali bisphenoxide of a dihydric sulfide.

15. A method for making an ether phthalimide of the formula,

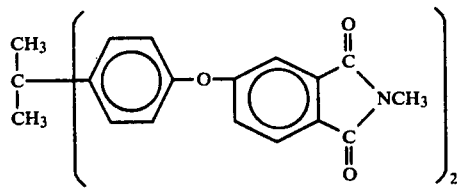

which comprises
(A) heating at 25° C. to 150° C. under substantially anhydrous conditions 4-nitro-N-methylphthalimide and the disodium salt of bisphenol-A in the presence of toluene and an effective amount of tetrabutyl ammonium bromide,
(B) agitating the resulting mixture with a precipitating or extractive organic solvent for said bisimide or allowing the mixture to cool and
(C) recovering the bisimide from the mixture of (B).

* * * * *